(12) United States Patent
O'Hara

(10) Patent No.: US 10,234,371 B2
(45) Date of Patent: Mar. 19, 2019

(54) METHOD AND APPARATUS FOR CHARACTERIZING SAND CONTROL INSERTS

(71) Applicant: RGL Reservoir Management Inc., Calgary (CA)

(72) Inventor: Michael O'Hara, Calgary (CA)

(73) Assignee: RGL Reservoir Management Inc., Calgary (CA)

( * ) Notice: Subject to any disclaimer, the term of this patent is extended or adjusted under 35 U.S.C. 154(b) by 144 days.

(21) Appl. No.: 14/941,303

(22) Filed: Nov. 13, 2015

(65) Prior Publication Data

US 2016/0139023 A1    May 19, 2016

Related U.S. Application Data

(60) Provisional application No. 62/080,076, filed on Nov. 14, 2014.

(51) Int. Cl.
*G01N 15/08* (2006.01)
*E21B 43/08* (2006.01)

(52) U.S. Cl.
CPC ......... *G01N 15/0826* (2013.01); *E21B 43/08* (2013.01); *G01N 2015/084* (2013.01)

(58) Field of Classification Search
CPC .......... G01N 15/0826; G01N 2015/084; E21B 43/08
USPC ............................................................. 73/38
See application file for complete search history.

(56) References Cited

U.S. PATENT DOCUMENTS

| | | | | |
|---|---|---|---|---|
| 2008/0128129 | A1* | 6/2008 | Yeh | E21B 17/02 166/275 |
| 2009/0151443 | A1* | 6/2009 | Slater | E21B 43/08 73/152.26 |
| 2009/0294128 | A1* | 12/2009 | Dale | E21B 33/127 166/306 |
| 2013/0312983 | A1* | 11/2013 | Robichaux | E21B 17/05 166/381 |

FOREIGN PATENT DOCUMENTS

CN    102261236 A    * 11/2011

OTHER PUBLICATIONS

Translation CN 102261236 A.*

* cited by examiner

*Primary Examiner* — Natalie Huls
*Assistant Examiner* — Monica S Young
(74) *Attorney, Agent, or Firm* — Santosh K. Chari; Blake, Cassels & Graydon LLP

(57) ABSTRACT

An open flow area test apparatus and test method for characterizing the performance of a sand control insert, such as slotted liner or wire-wrapped screen or other sand control apparatus. A sand control insert is set at or near the base of a pressure tight body, a sand pack is provided above the sand control insert, and a piston head applies a simulated overburden pressure to the sand pack. A test fluid is pumped through the sand control insert and differential pressures and sand flow through measured.

13 Claims, 13 Drawing Sheets

|  |  | Oil | Brine | Oil | Brine | Delta P Top of screen to Ref | | Delta P Mid sandpack to Ref Sys Pres. | | | | Delta P Inj. Head to Ref Sys Pressure, psi | Sandpack dealta p (psi), to top of screens |
|---|---|---|---|---|---|---|---|---|---|---|---|---|---|
| Date | Time (00:00) | Rate (L/Hr) | Rate (L/Hr) | Cum (liters) | Cum (liters) | Front Probe 1, psi | Back Probe 2, psi | Probe 1, psi | Probe 2, psi | Probe 3, psi | Probe 4, psi | | |
| Start | 20:15 | 0 | 0 | 0 | 0 | | | | | | | | |
| Day 1 | 13:05 | 2 | 6 | | | 0.52 | 0.62 | 0.63 | 0.53 | 0.81 | 0.52 | 1.52 | 0.44 |
| | 13:55 | 2 | 6 | | | 0.55 | 0.63 | 0.48 | 0.35 | 0.6 | 0.32 | 1.6 | 0.4 |
| | 14:55 | 2 | 6 | | | 0.16 | 0.31 | 0.52 | 0.37 | 0.45 | 0.28 | 1.62 | 0.38 |
| | 15:35 | 2 | 6 | 38.6 | 115 | 0.49 | 0.6 | 0.7 | 0.5 | 0.48 | 0.48 | 1.64 | 0.39 |
| Day 4 | 0:05 | 0 | 0 | | | | | | | | | | |
| | 17:12 | 4 | 12 | | | 0.55 | 0.27 | 1.21 | 1.24 | 1.26 | 1.1 | 3.41 | 1.68 |
| | 17:40 | 4 | 12 | | | 0.44 | 0.14 | 1.32 | 1.23 | 1.1 | 1.17 | 3.43 | 1.72 |
| | 18:12 | 4 | 12 | | | 0.48 | 0.26 | 1.38 | 1.27 | 1.23 | 1.1 | 3.51 | 1.7 |
| | 18:40 | 4 | 12 | 113.1 | 339 | 0.43 | 0.25 | 1.3 | 1.28 | 1.23 | 1.15 | 3.47 | 1.7 |
| | 18:45 | 0 | 0 | | | | | | | | | | |
| Day 5 | 1:46 | 6 | 18 | | | 0.51 | 0.22 | 1.89 | 1.87 | 1.72 | 1.64 | 5.26 | 2.63 |
| | 2:20 | 6 | 18 | | | 0.56 | 0.25 | 1.71 | 1.85 | 1.71 | 1.63 | 5.23 | 2.61 |
| | 2:47 | 6 | 18 | | | 0.56 | 0.25 | 1.72 | 1.65 | 1.64 | 1.56 | 5.28 | 2.69 |
| | 3:03 | 6 | 18 | 163.1 | 489 | 0.57 | 0.26 | 1.76 | 1.8 | 1.67 | 1.61 | 5.3 | 2.63 |
| Cummulative time (hours): | 46.22 | | | | | | | | | | | | |
| Cummulative oil (liters): | | | | 163.1 | | | | | | | | | |
| Cummuilative brine (liters): | | | | | 489 | | | | | | | | |

Figure 11

|  | Number of | Fraction % | Microns |
| --- | --- | --- | --- |
| Conglomerate (Cgl) | 0 | 0% | >2000 |
| Very Coarse (U) | 0 | 0% | 1410-2000 |
| Very Coarse (L) | 0 | 0% | 1000-1410 |
| Coarse (U) | 0 | 0% | 710-1000 |
| Coarse (L) | 0 | 0% | 500-710 |
| Medium (U) | 0 | 0% | 350-500 |
| Medium (L) | 24 | 24% | 250-350 |
| Fine (U) | 63 | 63% | 177-250 |
| Fine (L) | 13 | 13% | 125-177 |
| Very Fine (U) | 0 | 0% | 88-125 |
| Very Fine (L) | 0 | 0% | 62-88 |
| Silt | 0 | 0% | 0-61 |
| Total | 100 |  |  |

Figure 12

METHOD AND APPARATUS FOR CHARACTERIZING SAND CONTROL INSERTS

CROSS REFERENCE TO RELATED APPLICATIONS

This application claims the benefit of priority of U.S. Provisional Patent Application No. 62/080,076 filed Nov. 14, 2014, which is hereby incorporated by reference.

FIELD

The present disclosure relates generally to test methods and test apparatus. More particularly, the present disclosure relates to test methods and test apparatus for sand control inserts for oil and gas wells.

BACKGROUND

Oil and gas wells are sometimes drilled into subsurface reservoirs made of sandstone or sand. Sand control is often used to help keep the sand in the reservoir and out of the produced oil. This may be particularly important in horizontal wells in oil sands reservoirs.

Common sand control techniques include slotted liner, wire wrapped screen, and others.

Once installed subsurface, it may be difficult to evaluate the performance or relative performance of a sand control technique.

It is, therefore, desirable to provide a method and apparatus for characterizing sand control inserts.

SUMMARY

It is an object of the present disclosure to obviate or mitigate at least one disadvantage of previous methods and apparatus for characterizing sand screen inserts.

In a first aspect, the present disclosure provides an open flow area test apparatus for characterizing a sand control insert including a pressure tight body for containing a sand pack, a piston head for applying a pressure to the sand pack and adapted to allow flow of a pressurized test fluid into or out of the body, and a sand control insert junction adapted to allow insertion and removal of the sand control insert into the body, below the sand pack, wherein the sand control insert junction is adapted to allow flow of the pressurized fluid through the sand control insert and out of or into the body.

In an embodiment disclosed, the piston head has a piston face comprising a plurality of radial grooves for distribution of the test fluid into the sand pack.

In an embodiment disclosed, the piston face further comprising a plurality of axial groove for distribution of the test fluid into the sand pack.

In an embodiment disclosed, the open flow area test apparatus further comprising instruments for indicating pressure or flow rate or both.

In an embodiment disclosed, the sand control insert comprises wire-wrapped screen.

In an embodiment disclosed, the sand control insert comprises slotted liner.

In an embodiment disclosed, the sand control insert comprises pre-packed screen. In an embodiment disclosed, the sand control insert comprises precision punched screen.

In an embodiment disclosed, the sand control insert comprises metal-mesh screens.

In an embodiment disclosed, the sand control insert is selected from the group consisting of expandable sand screens, inflow control devices, selective isolation devices, and screen filtration.

In an embodiment disclosed, the open flow area test apparatus is adapted to characterize the sand control insert in a producer configuration, wherein the test fluid flows into the piston head and out of the sand control insert junction.

In an embodiment disclosed, the open flow area test apparatus is adapted to characterize the sand control insert in an injector configuration wherein the test fluid flows into the sand control insert junction and out of the piston head.

In a further aspect, the present disclosure provides a method for characterizing a sand control insert including providing an open flow area test apparatus having a pressure tight body for containing a sand pack, a piston head for applying a pressure to the sand pack and adapted to allow injection of a pressurized test fluid into the body, a sand control insert junction adapted to allow insertion and removal of the sand control insert into the body, below the sand pack, wherein the sand control insert junction is adapted to allow flow of the pressurized fluid through the sand control insert and out of the body, and instruments for indicating pressure or flow rate or both, selecting the sand control insert and installing the sand control insert into the open flow area test apparatus, deploying a sand pack into the open flow area test apparatus and saturating the sand pack with the test fluid, applying a simulated overburden pressure to the sand pack, injecting the test fluid into the sand pack at a flow rate and a flow pressure for a period of time to flow through the sand control insert, and measuring the performance of the sand control insert.

In an embodiment disclosed, the simulated overburden pressure is about 500 psia.

In an embodiment disclosed, the test fluid is a mixture of mineral oil and brine.

In an embodiment disclosed, the test fluid is separately injected mineral oil and brine.

In an embodiment disclosed, the test fluid is selected from the group consisting of natural gas, air, nitrogen, one or more light hydrocarbons in vapour state, steam, and combinations thereof. In an embodiment disclosed, the test fluid is steam. In an embodiment disclosed, the test fluid is a combination of steam and one or more light hydrocarbons in vapour state.

In an embodiment disclosed, measuring the performance of the sand control insert includes determining the retained permeability of the sand control insert, post-test.

In an embodiment disclosed, measuring the performance of the sand control insert includes collecting and measuring any amount and particle size distribution of sand produced from inside the sand control insert.

In an embodiment disclosed, measuring the performance of the sand control insert includes taking pressure readings from time to time, including one or more of at or near a top of the sand pack, at or near a midpoint of the sand pack, and adjacent to the sand control insert.

In an embodiment disclosed, measuring the performance of the sand control insert includes determining a pressure drop across the sand control insert from a pressure reading adjacent to the sand control insert.

In a further aspect, the present disclosure provides a method for characterizing a sand control insert including providing an open flow area test apparatus having a pressure tight body for containing a sand pack, a piston head for applying a pressure to the sand pack and adapted to allow a pressurized test fluid out of the body, a sand control insert junction adapted to allow insertion and removal of the sand control insert into the body, below the sand pack, wherein the sand control insert junction is adapted to allow flow of the pressurized fluid through the sand control insert into the sand pack, and instruments for indicating pressure or flow rate or both, selecting the sand control insert and installing the sand control insert into the open flow area test apparatus, deploying a sand pack into the open flow area test apparatus and saturating the sand pack with the test fluid, applying a simulated overburden pressure to the sand pack, injecting the test fluid into the sand pack at a flow rate and a flow pressure for a period of time to flow through the sand control insert, and measuring the performance of the sand control insert.

In an embodiment disclosed, measuring the performance of the sand control insert includes evaluation of injector sand control.

In an embodiment disclosed, measuring the performance of the sand control insert includes evaluation of open flow area efficiencies.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 11 is example test data of the present disclosure for a 12 gauge wire wrapped screen, indicating pressure drop and produced sand measurements;

FIGS. 12, 12A are example test data of the present disclosure for a 12 gauge wire wrapped screen, indicating post-test produced sand analysis including particle size distribution.

DETAILED DESCRIPTION

Generally, the present disclosure provides a method and apparatus for testing or characterizing sand control inserts.

Open Flow Area Test Apparatus

Figures 1, 1A:
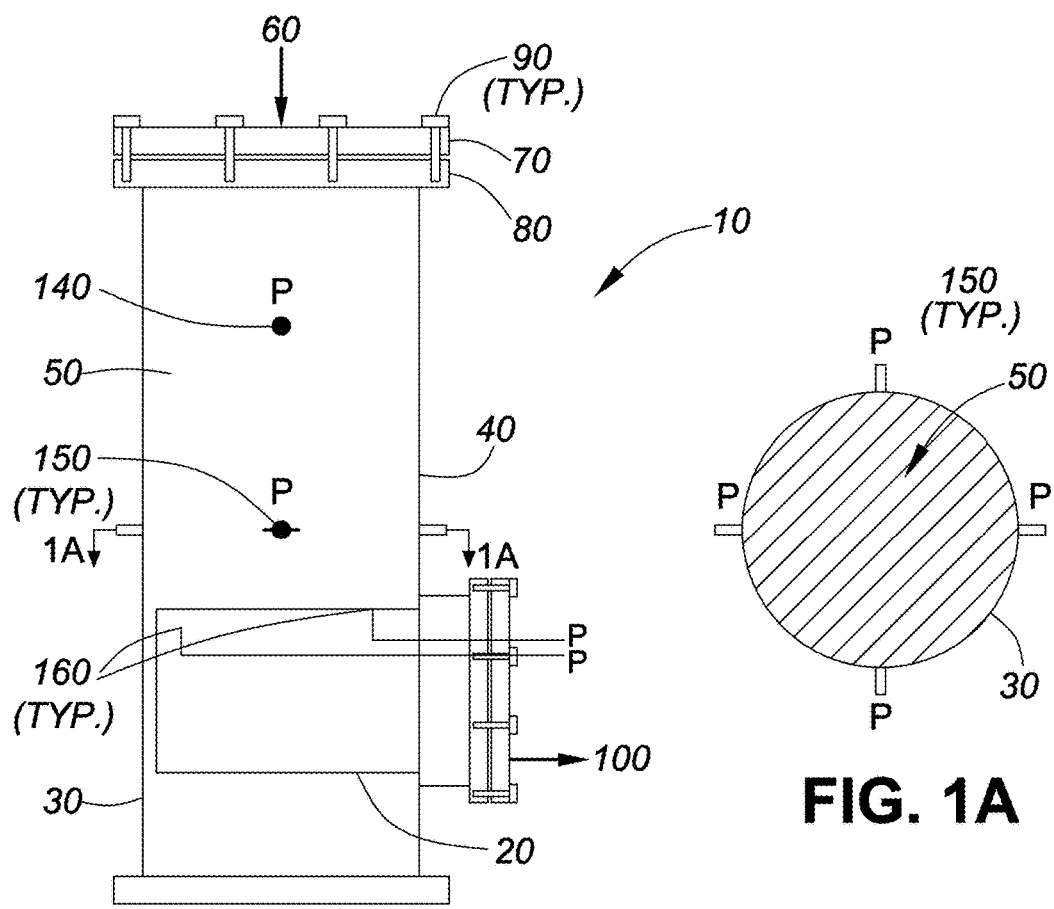
FIG. 1 is a simplified schematic of an open flow area test apparatus of the present disclosure.
FIG. 1A is a top view of FIG. 1, along section 1A-1A.
Figures 2, 2A:
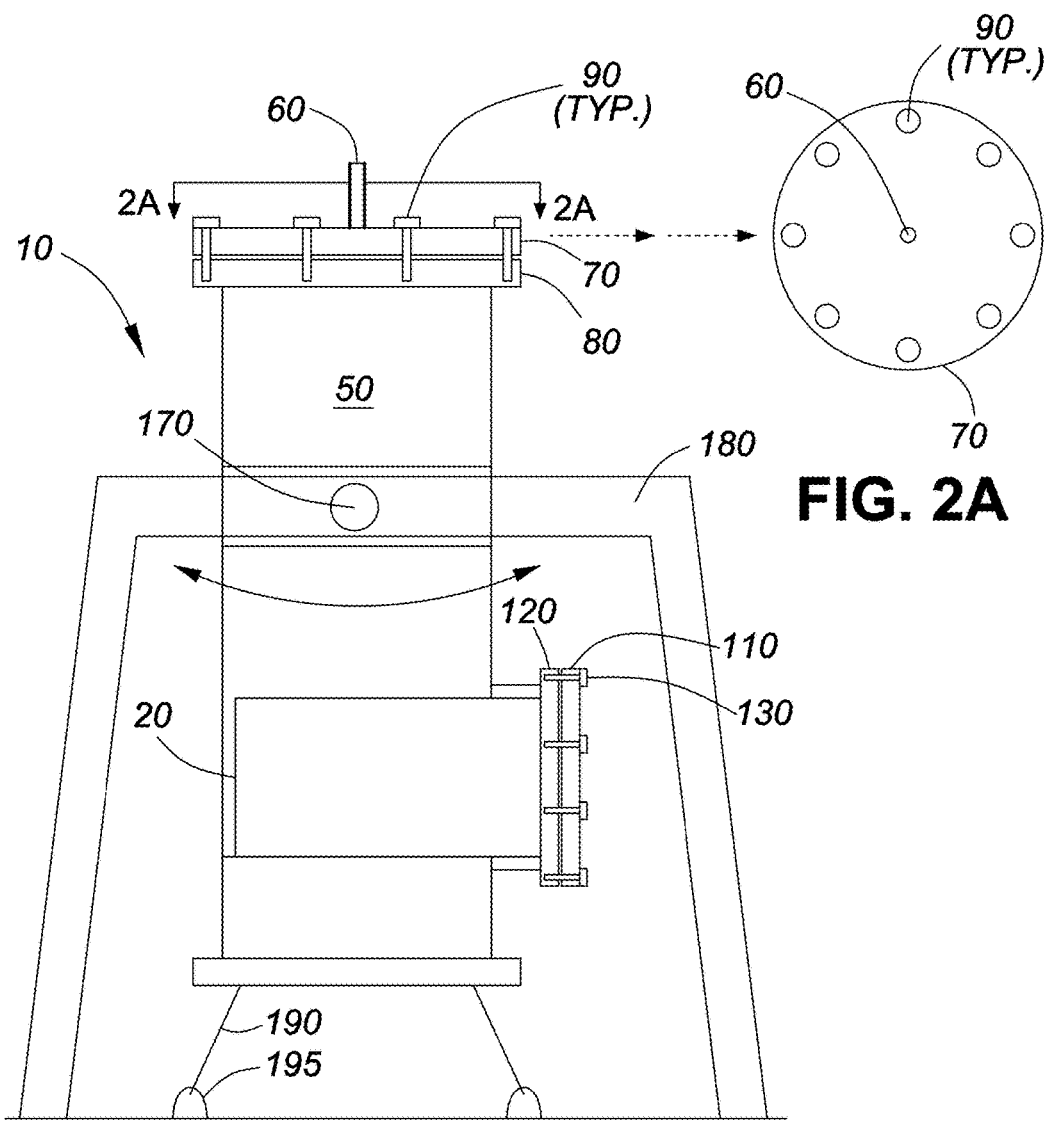
FIG. 2 is a simplified schematic of an open flow area test apparatus of the present disclosure.
FIG. 2A is a top view of FIG. 2, along section 2A-2A.

Referring to FIGS. 1 and 2, the open flow area (OFA) test apparatus 10 is a low pressure vessel used to evaluate sand control performance of a sand control insert 20, such as a screen or slotted liner etc., under a variety of conditions.

The open flow area test apparatus 10 includes a lower junction 30 to receive the sand control insert 20 and an upper body 40 designed to accommodate a sand pack 50. A port 60 is provided at or near the top of the body 40, for example as shown in removable plate 70. The plate 70 is connected to a flange 80 by bolts or studs 90. A port 100 is provided in the junction 30, for example as shown in removable cover 110. The cover 110 is connected to a flange 120 by bolts or studs 130.

In an embodiment disclosed, the sand pack 50 is about a 50 kg sand pack. In an embodiment disclosed, the sand pack 50 is a known sand with a known particle size distribution (PSD). In an embodiment disclosed, the sand pack 50 is sand from in situ locations, cleaned and PSD graded. In an embodiment disclosed, the body 40 and the junction 30 have an inner diameter (ID) of about 11 inches. In an embodiment disclosed, the sand control insert 20 is about 8 inches long, having an maximum outer diameter (OD) of about 7.625 inches.

Pressure taps may be located at various points across the sand pack 50. A pressure tap 140 is located at or near the top of the sand pack 50 to provide a sand pack top pressure. One or more pressure taps 150 (four shown) are located at or near the midpoint in the sand pack 50 to provide a sand pack middle pressure, spaced around the circumference of the body (at about 90 degrees with four pressure taps), to confirm radial sweep of the test fluids. One or more pressure taps 160 (two shown) are located at or near the interface between the sand pack 50 and the sand control insert 20 to provide a sand control insert pressure. Pressure indicators (gauges) or pressure transducers with pressure recorders are used to indicate or record the pressures (for example by computerized recording software) or both.

Figure 5:
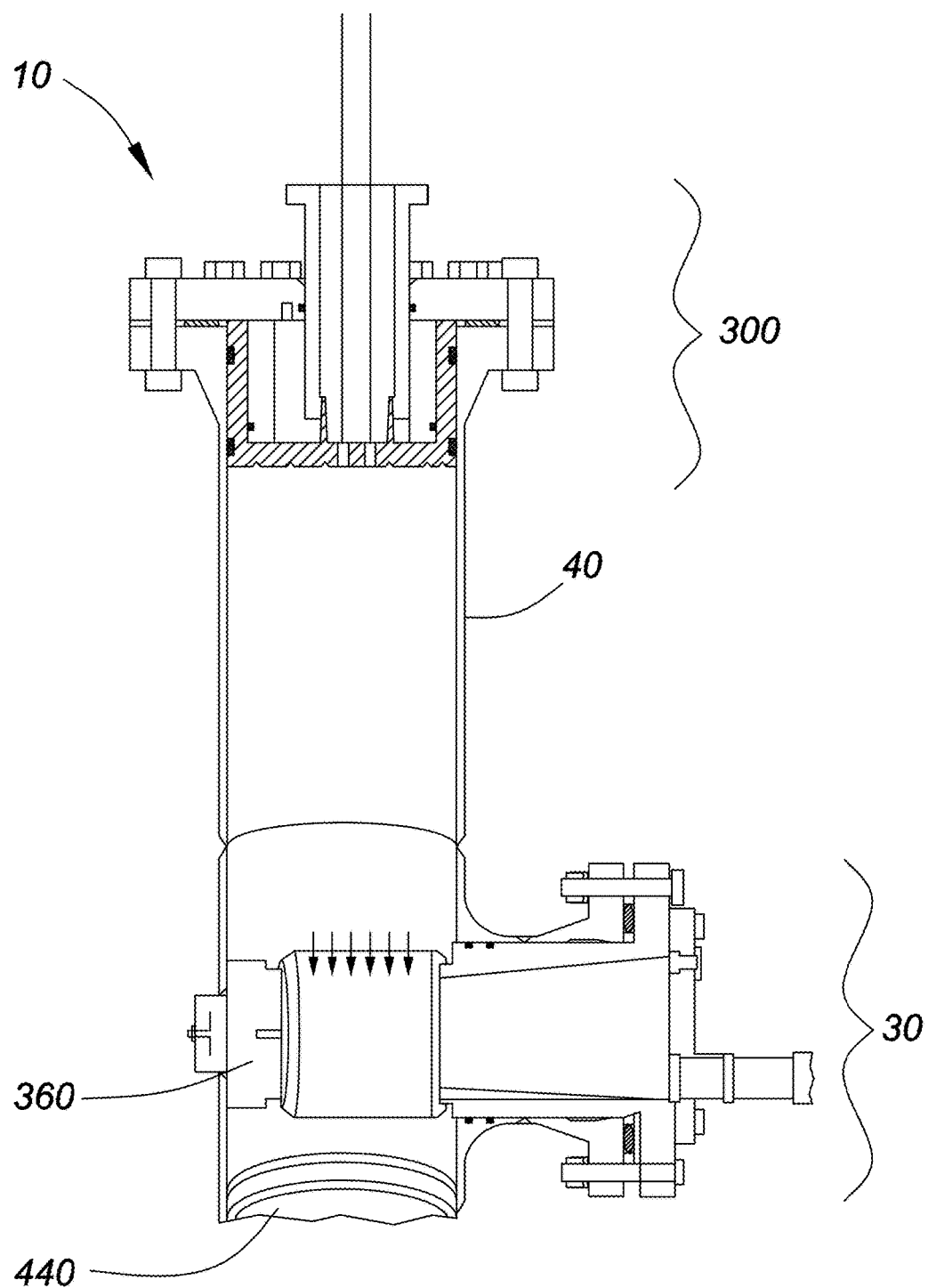
FIG. 5 is a cut-away perspective view of an open flow area test apparatus of the present disclosure.
Figure 6:
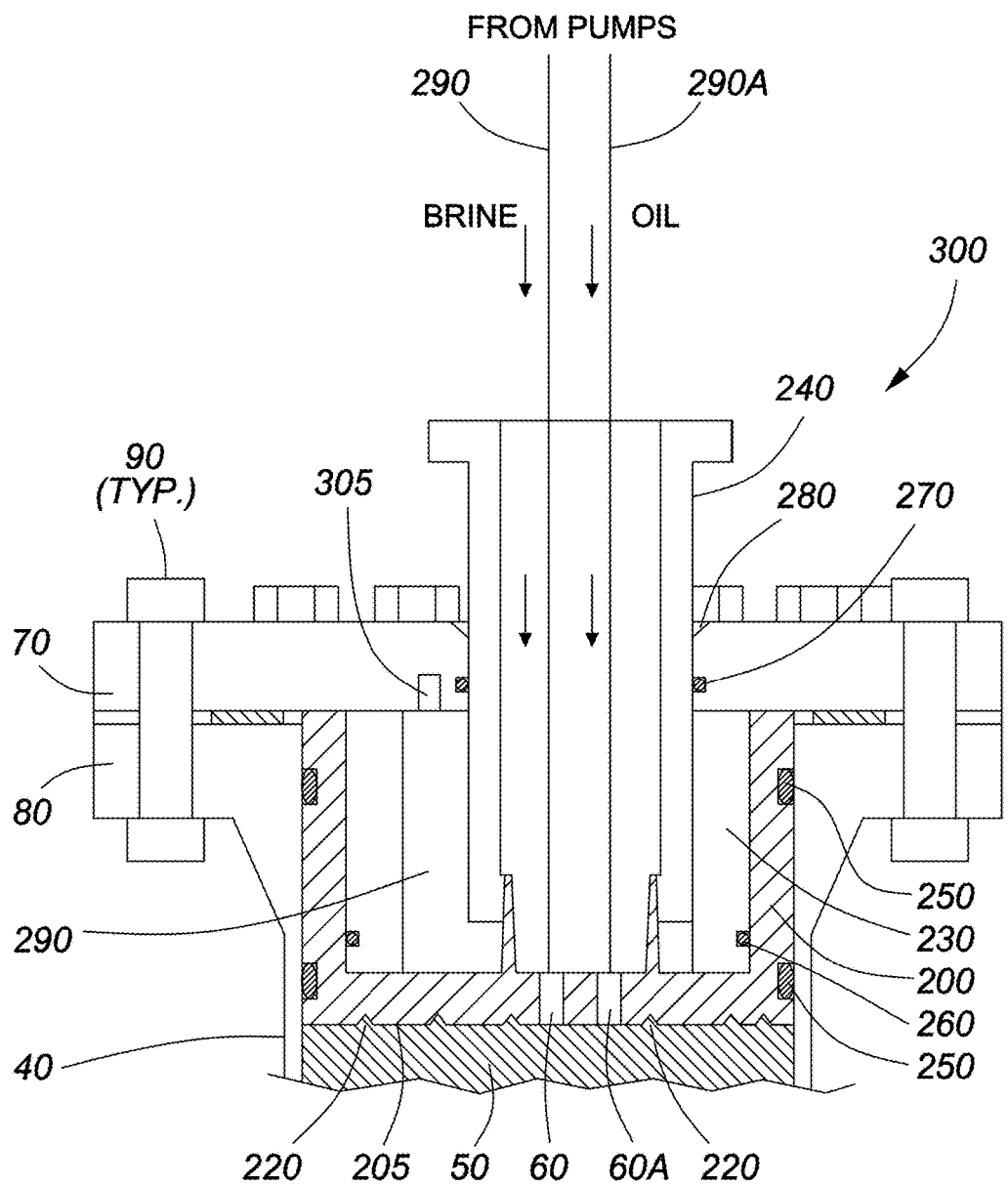
FIG. 6 is a detail of the open flow area test apparatus of FIG. 5, emphasizing the piston head.

Referring to FIGS. 5 and 6, a hydraulically activated piston 200 maintains a simulated overburden pressure on the sand pack 50, for example about 500 psi. The piston 200 travels within the body 40 (an upper portion of which may be machined inside to form a cylinder) within a piston guide 230 to allow for the compaction or loss of a portion of the sand pack 50. A piston tube 240 is connected to and moves with the piston 200. One or more seals 250 (two shown) seal between the outer diameter of the piston 200 and the inner diameter of the body 40. One or more seals 260 seal between the inner diameter of the piston 200 and the outer diameter of the piston guide 230 (one shown). One or more seals 270 seal between the outer diameter of the piston tube 240 and a port 280 in the plate 70 or between the outer diameter of the piston tube 240 and the inner diameter of the piston guide 230 (one o-ring seal shown at the plate 70). A sealed chamber 290 is thus formed between the piston 200 and the plate 70, and the application of fluid pressure to the chamber 290, for example via port 305 provides pressure to maintain a simulated overburden pressure on the sand pack 50. The combination of the piston 200 and the plate 70 with the port 280 act as a piston head 300. In an embodiment disclosed, the piston head 300 includes the piston guide 230 and the piston tube 240 (as in FIGS. 5, 6). In an embodiment disclosed, the piston head 300 may be made of stainless steel.

A test fluid, such as a mixture of mineral oil and brine are pumped into the body through the piston head 300 (via port 60). In an embodiment, the test fluid may be a mixture, co-injected, or separately injected (see FIGS. 5, 6, where separate conduits 290 and 290A are provided for mineral oil and brine to respective ports 60 and 60A).

Figures 3, 3A:
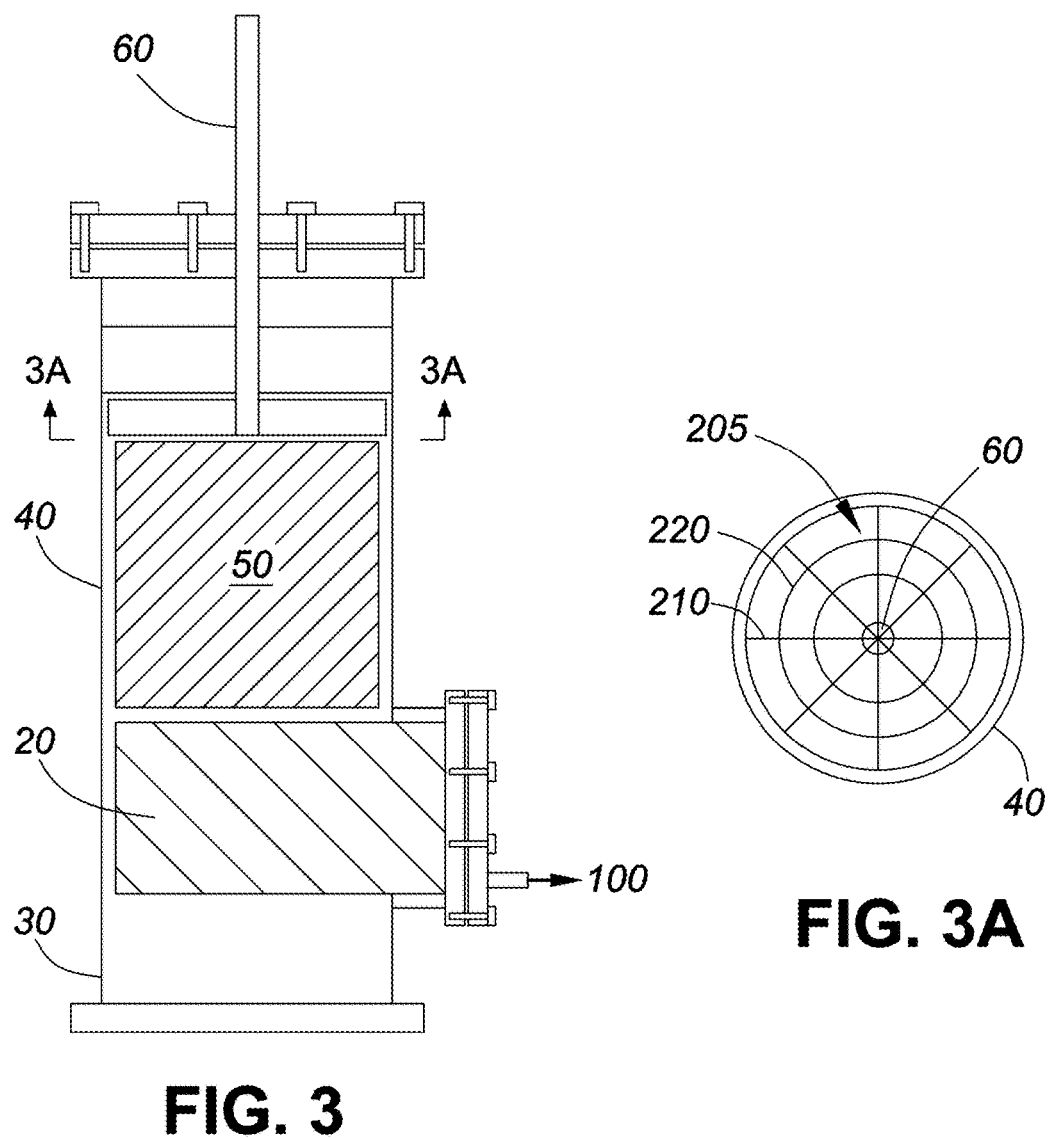
FIG. 3 is a simplified schematic of an open flow area test apparatus of the present disclosure.
FIG. 3A is a bottom view of FIG. 3, along section 3A-3A.
Figure 4:
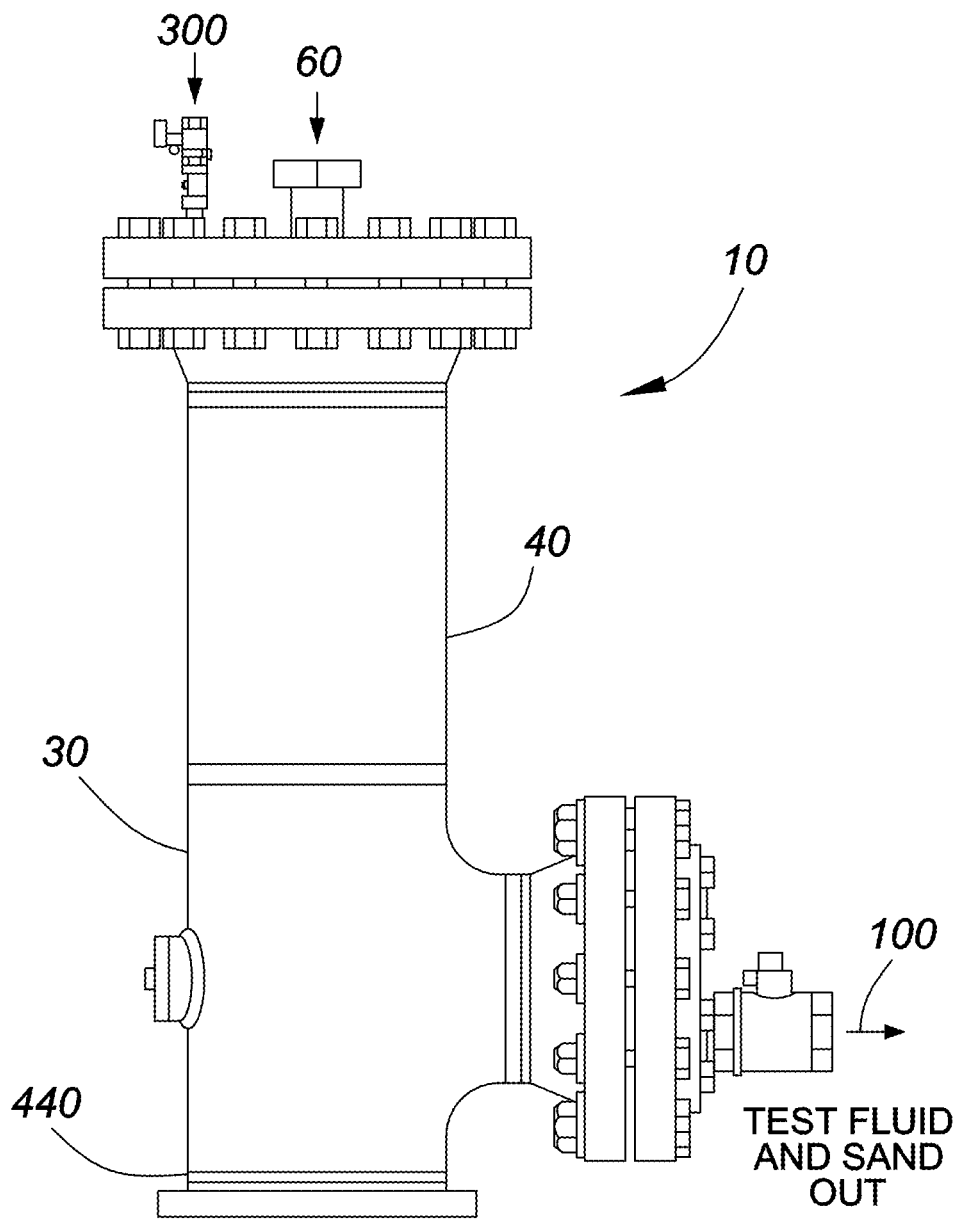
FIG. 4 is a side view of an open flow area test apparatus of the present disclosure.

The piston 200 has piston face 205 on the side facing the sand pack 50 (see FIGS. 3, 3A). In an embodiment disclosed, the piston face 205 includes one or more a radial grooves/channels 210. In an embodiment disclosed, the piston face 205 includes one or more radial grooves/channels 210 and one or more axial grooves/channels 220 (see FIGS. 3A, 6). This allows the test fluid (e.g. mineral oil and brine) to disperse horizontally and thus vertically more uniformly into the sand pack 50 (i.e. the test fluid fans out and is distributed horizontally and then is dispersed vertically into the sand pack 50).

The flow rate of the test fluid into the open flow area test apparatus 10 may be varied. Also, where the test fluid is a mixture or separately injected components, such as mineral oil and brine, the ratio of the components may be varied at least at one point during the test. In an embodiment disclosed the test fluid is separately injected about 20 cP mineral oil and about 1 percent brine. In an embodiment disclosed, the test fluid is a standardized fluid. In an embodiment disclosed, the test fluid is selected to approximate a reservoir fluid. In an embodiment disclosed, the test fluid is produced liquid hydrocarbon from in situ locations. In an embodiment disclosed, the test fluid is a $C_5$-$C_{30}$ hydrocarbon (hydrocarbon group having 5 to 30 carbon atoms) or mixtures thereof and brine. In an embodiment disclosed, the test fluid is injected at less than about 50 psig. In an embodiment disclosed, the test fluid may be selected from the group of steam, natural gas, air, nitrogen, or one or more light hydrocarbons in vapour state. In an embodiment disclosed, the test fluid may include the fluids, both liquid or vapours or both, known to a person skilled in the art to be representative of fluids encountered in oil and gas production from subsurface reservoirs.

A sand control insert 20 is mounted horizontally at or near the bottom of the body 40 below the sand pack 50. The ends of the sand control insert 20 are sealed such that the test fluid can only enter or exit the sand control insert 20 through an open flow area 340 and not the ends 350/350A (see FIGS. 9,10). Thus, the amount of test fluid or sand or both that enter the sand control insert 20 may be monitored or measured or both.

Figure 9:
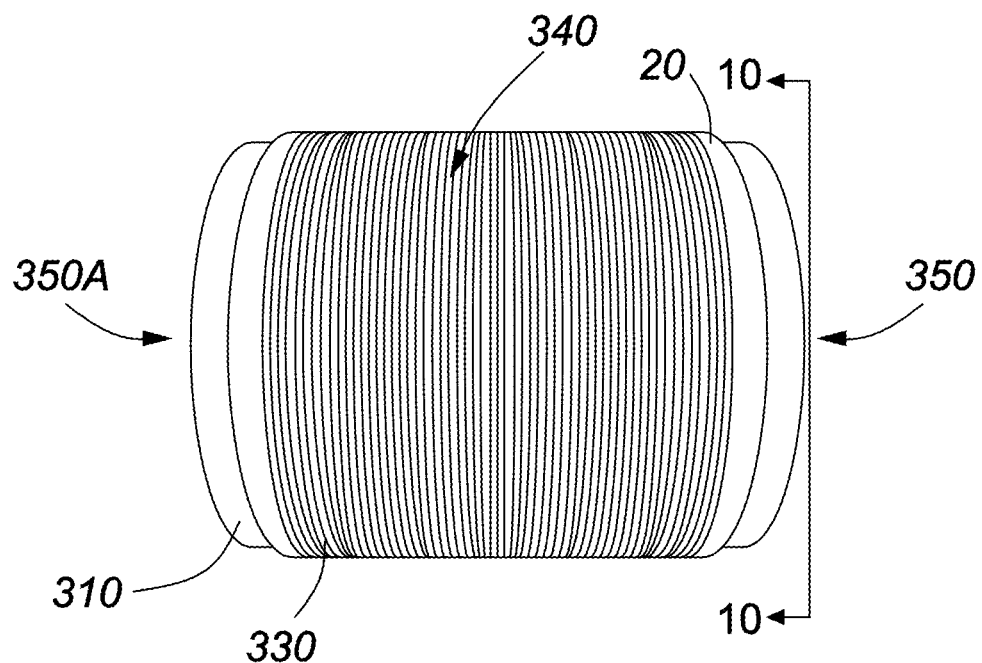
FIG. 9 is a wire-wrapped screen sand control insert of the present disclosure.
Figure 10:
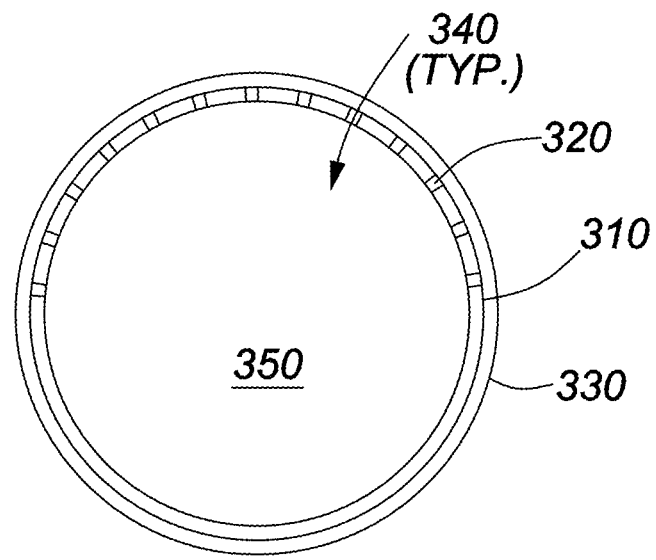
FIG. 10 is a horizontal end view of the wire-wrapped screen sand control insert of FIG. 9, along section 10-10.

The sand control insert 20 may be, for example, rolled or seamed slotted liner or wire wrap screen or other sand control insert or combinations thereof. The sand control insert 20 only allows test fluid and sand entry into the upper 180 degree circumference of the sand control insert. That is, the lower 180 degrees of the circumference is solid pipe, and the sand control technique is only applied to the upper 180 degrees of the circumference (see FIG. 10). If, for example, the sand control insert 20 is a slotted liner sand control insert, the upper 180 degrees is slotted and the lower 180 degrees would not be slotted. This allows test fluid and any produced sand to be recovered from the inside of the sand control insert 20. Referring to FIGS. 9, 10, an example of a sand control insert 20 in the form of a wire-wrapped screen (WWS) is shown. A pipe 310 having perforations 320 in an upper portion (upper 180 degrees shown) is wrapped with a wire wrap 330 providing an open flow area 340 through the wire wrap 330 and the perforations 320. At least one of the ends 350 and 350A of the pipe 310 are open so that the test fluid can flow through the sand control insert 20.

Figure 7:
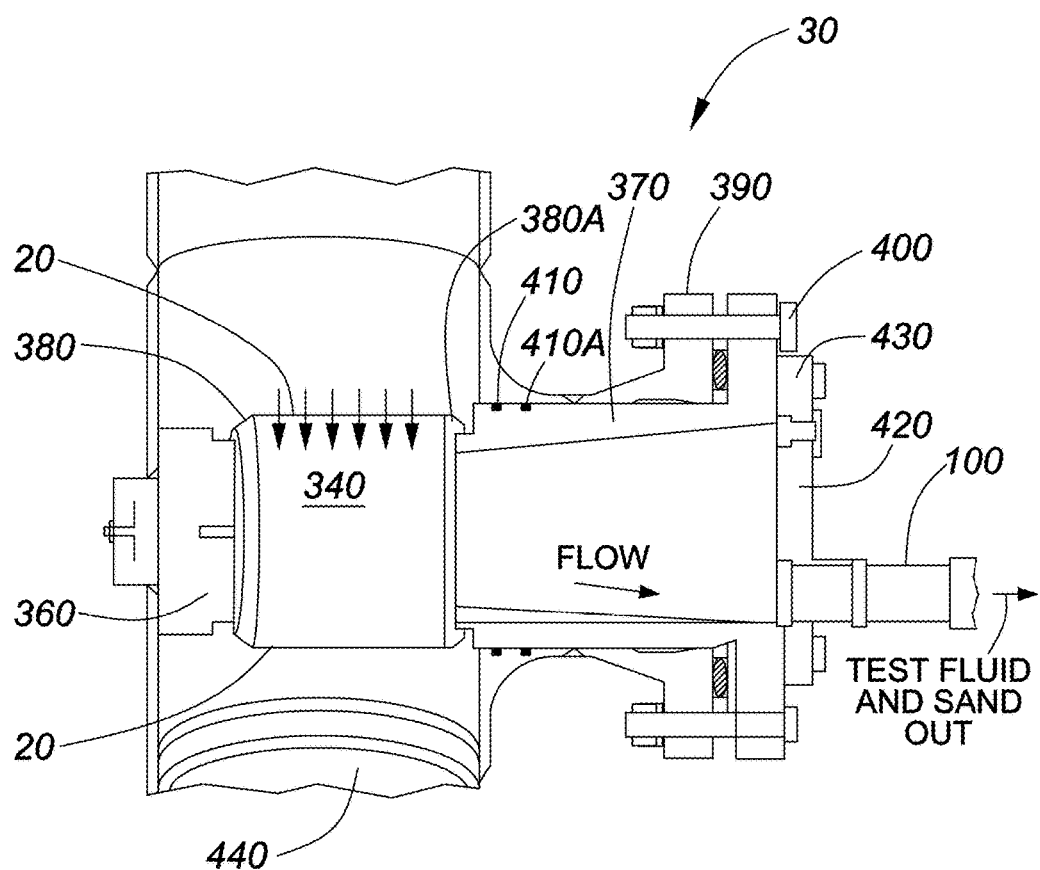
FIG. 7 is a detail of the open flow area test apparatus of FIG. 5, emphasizing the tee-junction.
Figure 8:
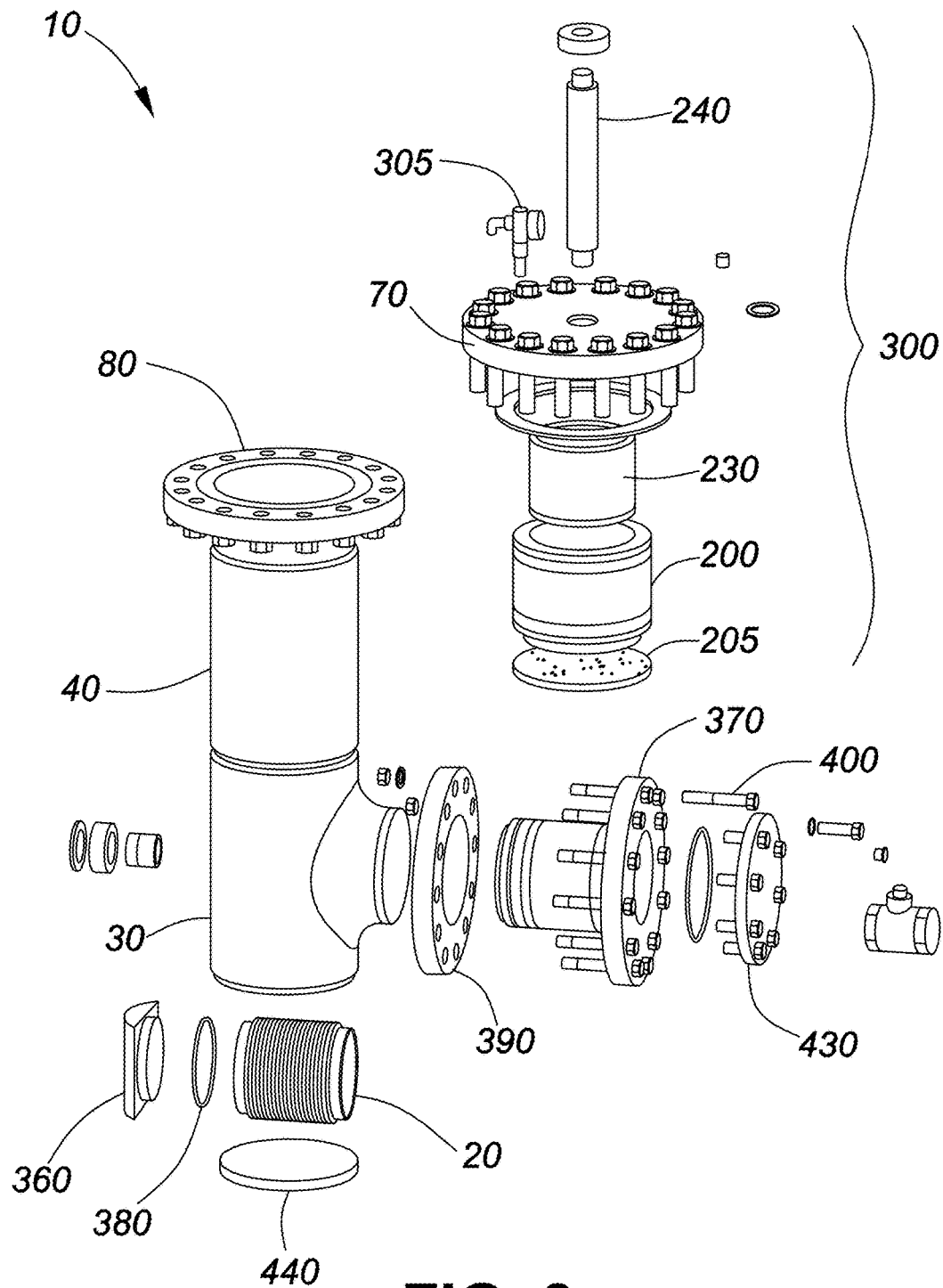
FIG. 8 is a disassembled view of an open flow area test apparatus of the present disclosure.

Referring to FIGS. 5, 7, the tee-junction 30 allows for insertion and removal of the sand control insert 20. The sand control insert 20 is removably secured between an inner assembly 360 and an outer assembly 370. Seals 380 and 380A provide a fluid seal between the sand control insert 20 and the inner assembly 360 and the outer assembly 370 respectively. The outer assembly 370 is connected to a flange 390 by bolts or studs 400. One or more seals 410 (two shown as seal 410 and seal 410A) seal between the outer diameter of the outer assembly 370 and the inner diameter of the flange 390. Thus the only path for the injected test fluid is through the open flow area 340. The bottom portion of the inner diameter of the outer assembly 370 is sloped to facilitate sand collection or flow. A plate 430, having a port 100, is attached to the outer assembly 370 by bolts or studs 430.

While shown as a tee-junction, other configurations may be used for the junction 30, for example but not limited to a cross-junction.

Referring to FIG. 2, the open flow area test apparatus 10 may be mounted on a gimbaled frame 180 that allows for the rotation of the body 40 about pivot pins 170 so the sand pack 50 may be more readily deployed into the body 40 and saturated with brine. The body 40 may be secured from pivoting by one or more members 190 extending between the body 40 and one or more anchors 195. The frame 180 may also be equipped with a winch or other hoist to allow for the safe removal of flanges or other heavy components.

Ancillary equipment includes associated storage for the mineral oil and brine test fluids, and pumps and pressure/temperature transducers.

Method

The open flow area test apparatus 10 is designed to evaluate a sand control insert 20 by measuring or one or more of the following:

Sand produced through the sand control insert 20;
Pressure drop across the sand control insert 20;
Retained permeability of the sand control insert 20, post-test; and
Open flow area 340 performance.

In order to evaluate or characterize the performance of the sand control insert 20, one may follow these steps using the open flow area test apparatus 10:

Select a sand control insert 20 and install the sand control insert 20 into the junction 30/body 40 of the open flow area test apparatus 10;

Deploy the sand pack 50 into the body 40 and saturate the sand pack 50 with the test fluids, for example mineral oil and brine, removing air from the sand pack 50 and wetting the sand pack 50;

Orient the body 40 of the open flow area test apparatus 10 vertically;

Apply a simulated overburden pressure to the sand pack 50 using the piston head 310, for example about 500 psia;

Inject test fluids into the sand pack 50 at injection flow rates through the piston head 310 for a period of time, while taking pressure readings from time to time, including one or more of at or near the sand pack top (pressure tap 140), at or near the midpoint in the sand pack (pressure tap 150), and adjacent to the sand control insert (pressure tap 160). The outlet of the sand control insert 20 (i.e. the inside of the sand control insert 20) is at atmospheric pressure, so the pressure reading from pressure tap 160 adjacent to the sand control insert 20 readily provides the pressure drop across the sand control insert 20. The test fluids flow through the sand pack 50, across the open flow area 340 of the sand control insert 20, and out the outlet port 100, and may be reused by filtration/separation, and circulation back to re-injection into the sand pack through the piston head;

After injecting test fluids for a predetermined period of time or predetermined volume of test fluids, the test is concluded, and the injection of test fluids is stopped.

One can then collect and measure the amount and particle size distribution (PSD) of the sand out (i.e. inside the sand control insert 20); and Determine the retained permeability of the sand control insert 20, post-test.

Figure 12A:
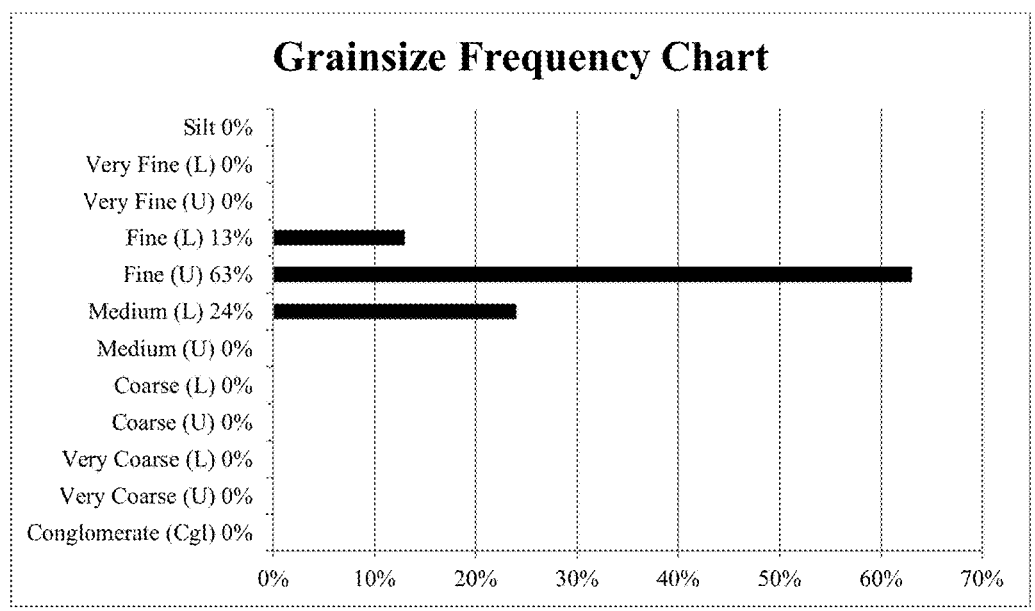
Figure 13:
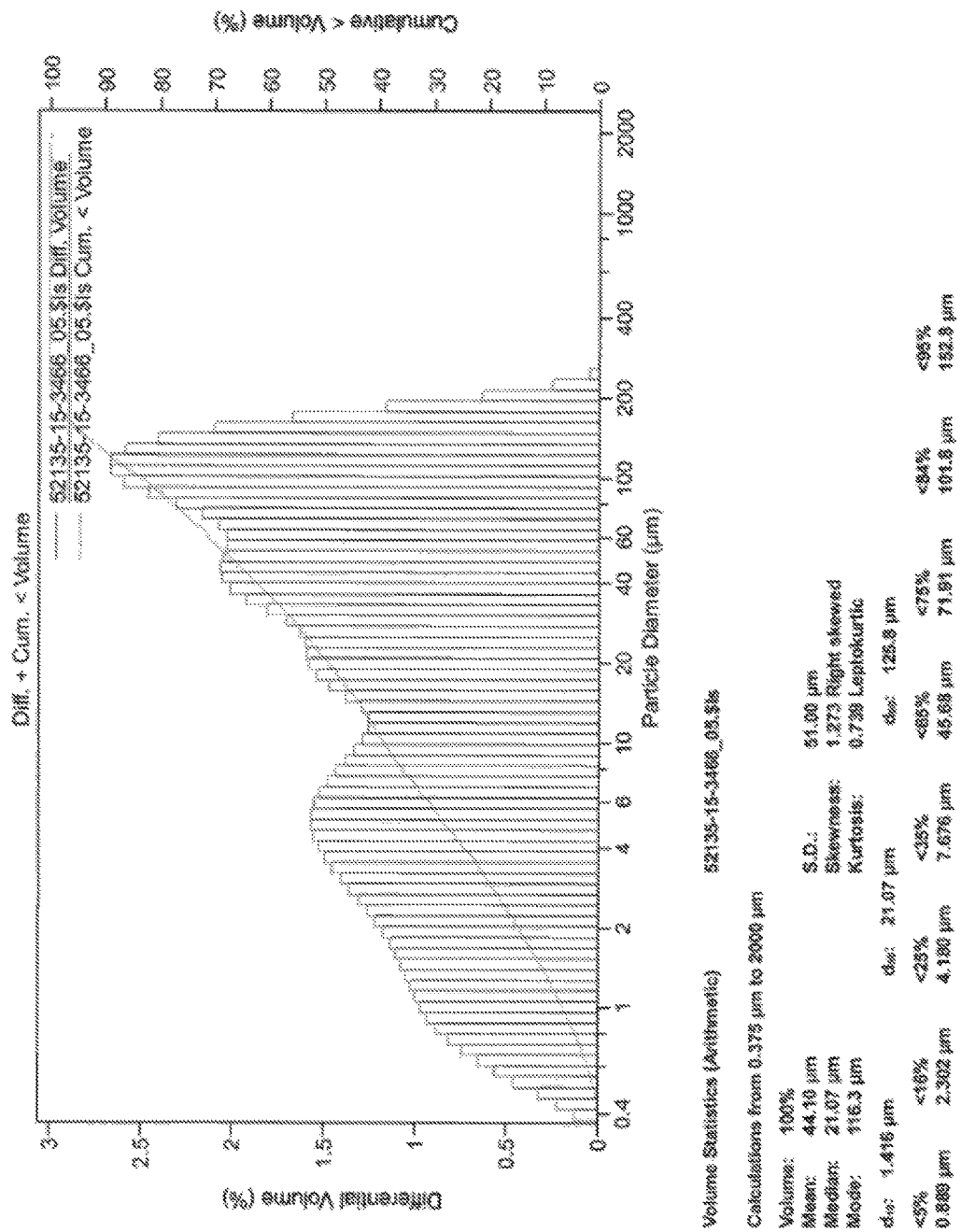
FIG. 13 is example test data of the present disclosure for a 12 gauge wire wrapped screen, indicating post-test produced sand analysis including particle size distribution.

Referring to FIGS. 11, and 12, 12A exemplary test results are shown for a 46 hour test of a 12 gauge wire-wrapped screen sand control insert 20. FIG. 12 indicates pressure drop and produced sand measurements. FIGS. 12, 12A indicate post-test produced sand analysis including particle size distribution. FIG. 13 indicates post-test produced sand analysis including particle size distribution.

This method may be repeated for other sand control inserts, and the performance of the sand control inserts may be relatively compared to one or more other sand control inserts.

In an embodiment disclosed, for example, one could conduct a 5 day test, starting with mineral oil for a day, then injecting brine and mineral oil at a ratio, for example 3:1 brine to mineral oil at a higher volumetric flow rate than the mineral oil was injected at the first day, and then finish with mineral oil for a day, again at the lower volumetric flow rate as was used for the first day, all while measuring the pressures and sand produced.

In the preceding description, the open flow area test apparatus 10 is described emphasizing characterizing the sand control insert in a producer configuration, wherein the test fluid flows into the piston head 300 via port 60, through the sand pack 50, through the open area 340 of the sand control insert 20, and out of the junction 30 via port 100. However, the open flow area test apparatus 10 may also be used to characterize the sand control insert in an injector configuration, by providing the test flow in a reverse direction. That is, wherein the test fluid flows into the junction 30 via port 100, through the open area 340 of the sand control insert 20, through the sand pack 50, and out of the piston head 300 via port 60.

In the preceding description, for purposes of explanation, numerous details are set forth in order to provide a thorough understanding of the embodiments. However, it will be apparent to one skilled in the art that these specific details are not required. In other instances, well-known structures are shown in block diagram form in order not to obscure the understanding.

In an embodiment disclosed, the present disclosure provides an open flow area test apparatus and test method for characterizing the performance of a sand control insert, such as slotted liner or wire-wrapped screen or other sand control apparatus. A sand control insert is set at or near the base of a pressure tight body, a sand pack is provided above the sand control insert, and a piston head applies a simulated overburden pressure to the sand pack. A test fluid is pumped through the sand control insert and differential pressures and sand flow through measured.

The above-described embodiments are intended to be examples only. Any dimensions shown are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. An apparatus for testing a sand control insert, the sand control insert comprising a generally tubular body having a wall with a plurality of perforations, the wall defining an open area, the apparatus comprising:
    a testing vessel having a first section and a second section;
        the first section defining a volume adapted to contain sand;
        the second section being adapted to receive the sand control insert;
        wherein the first and second sections are in fluid communication;
    a first port provided in the first section for passage of at least one pressurized fluid into the first section and through the sand;
    a second port provided in the second section for passage of fluids passing through the sand control insert out of the second section;
    a piston provided within the first section; the piston being sealed against the inner surface of the first section and adapted to travel in a direction toward the second section, whereby, when in use, the piston applies a pressure against the sand; and,
    a securing assembly, for positioning the sand control insert within the second section.

2. The apparatus of claim 1, wherein at least one pressurized fluid source is connected to the first port to supply the at least one pressurized fluid.

3. The apparatus of claim 2, wherein the first port is fluidly connected to the piston, whereby the at least one pressurized fluid enters the first section through the piston.

4. The apparatus of claim 2, wherein the second port is in fluid communication with the open area of the sand control insert, whereby the at least one pressurized fluid and sand passing through the sand control insert are drained through the second port.

5. The apparatus of claim 4, wherein the second port is connected to the securing assembly.

6. The apparatus of claim 5, wherein the second section includes an opening for receiving the securing assembly.

7. The assembly of claim 1 further comprising one or more pressure gauges for monitoring pressure within the testing vessel.

8. The apparatus of claim 1, wherein the piston is adapted to apply a pressure to the sand to simulate overburden in a wellbore.

9. The apparatus of claim 8, wherein the piston is adapted to apply a pressure of about 500 psia.

10. The apparatus of claim 1 further comprising a frame and wherein the testing vessel is rotatably connected to the frame.

11. The apparatus of claim 1, wherein the piston includes a piston face having a plurality of radial grooves.

12. The apparatus of claim 1 further comprising one or more pressure gauges for monitoring pressure within the sand in the first section.

13. The apparatus of claim 1, wherein the first section is vertically above the second section.

* * * * *